(12) United States Patent
Dugan

(10) Patent No.: US 7,294,332 B2
(45) Date of Patent: Nov. 13, 2007

(54) COMBINATION THERAPY (TEMOZOLOMIDE AND α-IFN) FOR ADVANCED CANCER

(75) Inventor: Margaret H. Dugan, Woodside, NY (US)

(73) Assignee: Schering Corporation, Kenilworth, NJ (US)

( * ) Notice: Subject to any disclaimer, the term of this patent is extended or adjusted under 35 U.S.C. 154(b) by 454 days.

(21) Appl. No.: 10/134,183

(22) Filed: Apr. 26, 2002

(65) Prior Publication Data

US 2002/0172662 A1 Nov. 21, 2002

Related U.S. Application Data

(63) Continuation of application No. 08/721,777, filed on Sep. 25, 1996, now abandoned.

(60) Provisional application No. 60/006,233, filed on Oct. 4, 1995.

(51) Int. Cl.
*A61K 38/21* (2006.01)
*A61K 38/19* (2006.01)
(52) U.S. Cl. ..................... 424/85.7; 424/85.4
(58) Field of Classification Search ............ None
See application file for complete search history.

(56) References Cited

U.S. PATENT DOCUMENTS

| | | | |
|---|---|---|---|
| 5,242,909 A | | 9/1993 | Teelmann |
| 5,503,828 A | * | 4/1996 | Testa et al. ............ 424/85.7 |
| 5,610,220 A | | 3/1997 | Klimmek et al. |
| 5,824,346 A | * | 10/1998 | Dugan .................. 424/649 |

FOREIGN PATENT DOCUMENTS

| WO | WO 89/06139 | 7/1989 |
|---|---|---|
| WO | WO 90/06135 | 6/1990 |

OTHER PUBLICATIONS

Wadlet et al. Biological agents as biochemical modulators:pharmacological basis for the interaction of cytotoxic chemotherapeutic drugs and interferon (1994). Cancer Chemother. Pharmacol. vol. 35, pp. 21-30.*
Bleehen et al. Cancer Research Campaign Phase II Trial of Temozolomide in Metastatic Melanoma (1995). J. Clin. Oncology. vol. 13 pp. 910-913.*
Newlands et al. Phase I trial of temozolomide (CCRG81045: M7B 39831: NSC362856) (1992). Br. J. Cancer, vol. 65, pp. 287-291.*
Sparano et al. Clinical and Pharmacological studies of interferon and chemotherapy in gastrointestinal and breast cancer (1993). Int. J. Cli. Pharm. Res. vol. 13 pp. 1-9.*
Atkins M.B. et al., "Phase II Pilot Trial of Concurrent Biochemotherapy with Cisplatin, Vinblastine, Temozolomide (CVT), Interleukin-2 (IL-2) and Interferon alpha-2b (IFN) in Patients with Metastatic Melanoma", Meeting Abstract of Proc. Annu. Meet. Am. Soc. Clin. Oncol, 2001:1391.

Tsioulias G.J. et al., "Salvage metastasectomy improves survival in stage IV Melanoma Patients treated with concurrent biochemotherapy", Meeting Abstract of Proc. Annu. Meet. Am. Soc. Clin. Oncol, 2001:1440.
Gibbs P. et al., "A multicenter phase II study of modified biochemotherapy (BCT) for stage IV melanoma incorporating temozolomide, decrescendo interleukin-2 (IL-2) and GM-CSF", Meeting Abstract of Proc. Annu. Meet. Am. Soc. Clin. Oncol, 2000;19:A2255.
Gonzalez R. et al., "A preliminary analysis of a multicenter phase II study of biochemotherapy with temozolomide, cisplatin, interleukin-2, alpha-interferon, and granulocyte macrophage colony stimulating factor (GM-CSF) for stage IV melanoma", Meeting Abstract of Chemotherapy Foundation Symposium XVII. 11/3-6/99. *Cancer Invest.*, 2000;18 (Suppl. 1): Abstract 78.
Kersen M-J. et al., "Combined immunotherapy with Gm-CSF, IL-2 and IFN? Allows dose escalation of temozolomide with prevention of lymphocytopenia and brain metastases in metastatic malignant melanoma", Meeting Abstract of Proc. Annu. Meet. Am. Soc. Clin. Oncol, 2000;19:A2244.
Kirkwood J.M. et al., "Phase I study of temozolomide in combination with interferon alpha-2b in metastatic malignant melanoma", Meeting Abstract of Proc. Annu. Meet. Am. Soc. Clin. Oncol, 1997;16:A1767.
Ruggero R. et al., "TMZ plus IFN-2 alpha in metastatic melanoma; preliminary evaluation of a multicenter phase II study of the Italian Melanoma Intergroup", Am. Soc. Clin. Oncol. 2002, Abstract No. 1388.
Danson S. et al., "A randomized study of temozolomide (TMZ) alone, with interferon (TMZ-IFN) or with thalidomide (TMZ-THAL) in metastatic malignant melanoma (MMM)", Am. Soc. Clin. Oncol. 2002, Abstract No. 1369.
Garcia Martin M. et al., "Phase II multicenter study of temozolomide in combination with interferon alpha-2b in metastatic malignant melanoma", Am. Soc. Clin. Oncol. 2002, Abstract No. 1389.
Weber R. et al., "A phase II trial of Temozolomide, GM-CSF, IFN-2 alpha, IL-2 in patients with metastatic melanoma", Am. Soc. Clin. Oncol. 2002, Abstract No. 2791.
*Physicians'Desk Reference*, Electronic Edition 2002, PDR Entry for Temoar (Temozolomide).
Goodman and Gilman's *The Pharmacological Basis of Therapeutics*, Eighth Edition, pp. 1205-1207 (1990).
Ridolfi, R. et al., "TMZ plus IFN-2 alpha in metastatic melanoma; preilminary evaluation of a multicenlar phase II study of the Italian Melanoma Intergroup", Am. Soc. Clin. Oncol. 2002, Abstract No. 1388.

(Continued)

*Primary Examiner*—Christine J. Saoud
*Assistant Examiner*—Jegatheesan Seharaseyon
(74) *Attorney, Agent, or Firm*—Sandy Zaradic

(57) ABSTRACT

There is disclosed a method for treating advanced cancer in patients in need of such treating. Temozolomide and alpha interferon are administered in combination in amounts sufficient to achieve a clinical response.

16 Claims, No Drawings

OTHER PUBLICATIONS

Yung, W.K.A. et al., "A combination of temozolomide and interferon-A in recurrent malignant gllomas, a phase II study", Fourth Annual Meeting of the Society for Neuro-Oncology, Nov. 17-21, 1999, Scottsdale, Arizona; Neuro-Oncology, Oct. 1999, 293-294.

Abrams et al., "New Chemotherapeutic agents for breast cancer," *Cancer*, 74(3 Suppl.): 1164-1176 (1994).

Carter et al., "Responses of human melanoma, ovarian, and colon tumor xenografts nude mice to oral temozolomide," Proc Annu Meet Am Assoc Cancer Res, 35:297, Abstract 1769 (1994).

* cited by examiner

COMBINATION THERAPY (TEMOZOLOMIDE AND α-IFN) FOR ADVANCED CANCER

This application is a continuation of U.S. Ser. No. 08/721,777 filed Sep. 25, 1996, now abandoned, which claims priority from U.S. Provisional Application No. 60/006,233 filed Oct. 4, 1995.

Despite the numerous advances in cancer treatment, the well-known life style changes that can greatly reduce the risk of cancer, and the early warning signs that some cancers provide, many patients still develop advanced cancer for which no conventional therapies are available that offer any reasonable hope of cure or significant palliation. This invention is the use of two known anti-tumor agents in combination therapy to provide a positive effect on such advanced cancers. It is also expected that the combination therapy will allow the administration of the two anti-tumor agents in quantities that will not result in intolerable side effects.

Temozolomide is known for its anti-tumor effects. For example, in one study clinical responses were achieved in 17% of patients having advanced melanoma (Newlands ES, et al. Br J Cancer 65 (2) 287-2981, 1992). In another study a clinical response was achieved in 21% of patients with advanced melanoma (Journal of Clinical Oncology, Vol 13, No. 4 (April), 1995, pp 910-913). However, temozolomide is not always effective and has dose-limiting side effects, such as hematologic toxicity, myelosuppression, anemia, leukopenia, etc.

Alpha interferon is also known to have anti-cancer effects. See, for example, Ernstoff et al., Intravenous (IV) Recombinant α-2 Interferon in Metastatic Melanoma, Proc ASCO 2:57 (C-222), 1983. However this treatment is not always effective and sometimes results in intolerable side effects related to the dosage and duration of therapy.

There is a need for a method for treating advanced cancers with higher response rates or reduced side effects, or both.

SUMMARY OF THE INVENTION

This invention may be summarized as a method for treating advanced cancer in patients in need of such treating comprising administering temozolomide and alpha interferon in amounts sufficient to achieve a clinical response. The temozolomide is administered to the patient in combination with the alpha interferon, that is, the temozolomide and alpha interferon doses are administered during the same period of time. Preferred specific dosing schedules are given below.

DETAILED DESCRIPTION

All references cited herein are incorporated herein by reference.

The term "temozolomide" is intended to mean a compound having the formula.

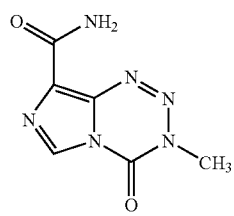

One chemical name for temozolomide is 3,4-dihydro-3-methyl-4-oxoimidazo-[5,1-d]1,2,3,4-tetrazin-8-carboximide. The synthesis of temozolomide is well known. See, for example, Stevens et al., J. Med. Chem, 1984, 27, 196-201 and Wang et al., J. Chem. Soc., Chem. Commun., 1994, pp 1687-1688.

The term "alpha interferon" as used herein means the family of highly homologous species-specific proteins that inhibit viral replication and cellular proliferation and modulate immune response. Typical suitable alpha interferons include but are not limited to recombinant interferon alpha-2b such as Intron-A interferon available form Schering Corporation, Kenilworth, N.J., recombinant interferon alpha-2a such as Roferon A interferon available from Hoffmann-La Roche, Nutley, N.J., recombinant interferon alpha-2C such as Berofor alpha 2 interferon available from Boehringer Ingelheim Pharmaceutical, Inc., Ridgefield, Conn., interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain. or a consensus alpha interferon available from Amgen, Inc., Newbury Park, Calif., or interferon alpba-n3 a mixture of natural alpha interferons made by Interferon Sciences and available from the Purdue Frederick Co., Norwalk, Conn., under the Alferon Tradename. The use of interferon alpba-2a or alpha 2b is preferred. interferon alpha 2b is most preferred. The manufacture of interferon alpha 2b is described in U.S. Patent No. 4,530,901.

Advanced cancers treatable by this invention include malignant melanoma, malignant metastasized melanoma, cancer of the lung, cancer of the breast, brain cancer, ovarian cancer, cancer of the head and/or neck, sarcoma, prostate cancer, and other cancers known to be at least partially responsive to alpha interferon or temozolomide treatment, that have advanced to a stage where conventional therapy is unlikely to provide a cure.

A person suffering from advanced cancer may exhibit one or more of the following signs or symptoms:
(a) presence of cancerous tumor,
(b) fatigue,
(c) pain,
(d) decreased performance status from tumor burden, and
(e) the well known symptoms associated with each specific cancer.

To practice the invention, temozolomide and alpha interferon are administered to the patient exhibiting one of more of the above signs or symptoms in amounts sufficient to eliminate or at least alleviate one or more of the signs or symptoms.

The preferred dosage of temozolomide for practicing the combination therapy of this invention is 50 to 400 mg per $m^2$ of the patient's body surface area per day, more preferably 75 to 300 mg/$m^2$ and most preferably 100 to 200 mg/$m^2$/day. It is preferred that the daily dosage of temozolomide be administered once per day for a 2 to 10 day period, more preferably for a 3 to 8 day period and most preferably for a 5 day period. The temozolomide dosing periods may be repeated in cycles of 28 to 42 days, more perferably 28 to 35 days, and most preferably 28 days. That is, 28 to 42 days after the first day of temozolomide administration, another temozolomide administration period may be started.

Alternatively the temozolomide may be administered for a much longer period at reduced dosage. For example, the temozolomide could be administered daily for 11 days to six weeks at a dosage of 50 to 150 mg/$m^2$/day.

Temozolomide may be administered orally in capsule form wherein it is admixed with conventional pharmaceutical carriers. Preferred temozolomide capsule formulations are:

| Ingredient | mg/Capsule | | | |
|---|---|---|---|---|
| temozolomide | 5 | 20 | 100 | 250 |
| Anhydrous Lactose NF | 132.8 | 182.2 | 175.7 | 154.3 |
| Sodium Starch Glycolate NF | 7.5 | 11.0 | 15.0 | 22.5 |
| Colloidal Silicon Diozide NF | 0.2 | 0.2 | 0.3 | 0.7 |
| Tartaric Acid NF | 1.5 | 2.2 | 3.0 | 9.0 |
| Steric Acid NF | 3.0 | 4.4 | 6.0 | 13.5 |
| Capsule Size* | 3 | 2 | 1 | 0 |

*White opaque, preservative-free, two-piece hard gelatin capsules

It is especially preferred that the patient fast from all food or drink, except water, for four hours before temozolomide administration and for two hours after.

The alpha interferon is preferably administered by intravenous or subcutantous injection beginning on day one of the first temozolomide administration period. However, unlike the temozolomide, the alpha interferon is administered more or less regularly throughout the combination therapy. The alpha interferon may be administered 1 to 7 times per week, more preferably 2 to 5 times per week, and most preferably three times per week or every other day. The amount of alpha interferon per dose may be 1 million to 25 million international units (IU) per $m^2$ of patient's body surface area, more preferably 5 million to 15 million $IU/m^2$ and most preferably 7.5 million to 12.5 million $IU/m^2$.

The treatment may be continued until a clinical response is achieved or until intolerable side effects are encountered. The dosages of temozolomide and/or alpha interferon may be increased with each new treatment cycle, provided intolerable side effects are not encountered. The dosages may also be decreased, if intolerable side effects are encountered.

A common, but tolerable, side effect of temozolomide is nausea and vomiting. This can be alleviated by administering an anti-emetic in conjunction with the temozolomide. It is preferred that the anti-emetic Ondansetron be given p.o. in a dose of about 8 mg about 30 minutes before temozolomide administration. Of course other anti-emetics such as Haldol, Benadryl, and Ativan may also be used as needed.

A common, but usually tolerable, side effect of alpha interferon is flu-like symptoms. These can usually be alleviated with acetaminophen and other common aspirin-like medicines.

Of course, other forms of administration of both active ingredients, as they become available, are contemplated, such as by nasal spray, transdermally, by suppository, by sustained release dosage form, by IV injection, etc. Any form of administration will work so long as the proper dosages are delivered without destroying the active ingredient.

The effectiveness of treatment may be determined by controlled clinical trials. Patients having advanced cancer with measurable or evaluable tumors will be included in the study. A measurable tumor is one that can be measured in at least two dimensions such as a lung tumor surrounded by aerated lung, a skin nodule, or a superficial lymph node. An evaluable tumor in one that can be measured in one dimension such as a lung tumor not completely surrounded by aerated lung or a palpable abdominal or soft tissue mass that can be measured in one dimension. Tumor markers which have been shown to be highly correlated with extent of disease will also be considered to provide an evaluable disease, such as PSA for prostate cancer, CA-125 for ovarian cancer, CA-15-3 for breast cancer, etc.

The tumor will be measured or evaluated before and after treatment by whatever means provides the most accurate measurement, such as CT scan, MRI scan, Ultrasonography, etc. New tumors or the lack thereof in previously irradiated fields can also be used to assess the anti-tumor response. The criteria for evaluating response will be similar to that of the WHO Handbook of Reporting Results of Cancer Treatment, WHO Offset Publication 1979, 49-World Health Organization, Geneva. The following results are defined for uni- and bi-dimensionally measurable tumors.

Complete Response: Complete disappearance of all clinically detectable malignant disease determined by two observations not less than four weeks apart.

Partial Response: (a) for bidimensionally measurable tumors, a decrease of at least 50% in the sum of the products of the largest perpendicular diameters of all measurable tumors as determined by two observations not less than four weeks apart. (b) for unidimensionally measurable tumors, a decrease by at least 50% in the sum of the largest diameters of all tumors as determined by two observations not less than four weeks apart. In cases where the patient has multiple tumors, It is not necessary for all tumors to have regressed to achieve a partial response as defined herein, but no tumor should have progressed and no new tumor should appear.

Stable Disease: (a) for bidimensionally measurable tumors, less than a 50% decrease to less than a 25% increase in the sum of the products of the largest perpendicular diameters of all measurable tumors. (b) for unidimensionally measurable tumors, less than a 50% decrease to less than a 25% increase in the sum of the diameters of all tumors. For (a) and (b) no new tumors should appear.

No clinical response, i.e. progressive disease in defined as an increase of more than 50% in the product of the largest perpendicular diameters for at least one bidimensionally measurable tumor, or an increase of more than 25% in measurable dimension of at least one unidimensionally measurable tumor.

For patients having both uni- and bi-dimensionally measurable tumors, the overall response will be determined in accordance with the following table.

| Response in bidimensionally measurable disease | Response in unidimensionally measurable disease | Overall Response |
|---|---|---|
| PD | any | PD |
| Any | PD | PD |
| SD | SD or PR | SD |
| SD | CR | PR |
| PR | SD or PR or CR | PR |
| CR | SD or PR | PR |
| CR | CR | CR |

Abbreviations:
PD: Progressive Disease
CR: Complete Response
PR: Partial Response
SD: Stable Disease Of course elimination or alleviation of other known signs or symptoms of advanced cancer, especially those listed previously can also be used to evaluate the effectiveness of this invention.

The advanced cancers should be evaluated, i.e. tumors measured, etc., no more than 14 days before the start of the treatment. These cancers should be reevaluated about 28 days after day 1 of administration of the first doses of temozolomide and alpha interferon. Twenty eight days after this initial administration another administration period may be performed, and evaluations performed 28 days after the start of this second cycle. The treatment cycles may be continued until a clinical response is achieved or unacceptable toxicity is encountered.

Another aspect of this invention is the treatment of advanced cancer with reduced side effects normally associated with temozolomide and alpha interferon. It is believed that this objective can be achieved by administration of lower doses of the two active ingredients or by shorter duration of dosing brought about by the synergistic effect of the combination.

The most serious side effect of temozolomide is hematologic toxicity. Dose limiting toxicity for temozolomide is defined herein as CTC Grade 4 neutropenia (absolute neutrophil count, including bands, of less than $0.5 \times 10^3/mm^3$) which is not resolved in five days or CTC Grade 4 anemia (hemoglobin of less than 6.5 g/dl), or CTC Grade 3 thrombocytopenia (platelet count of less than $50 \times 10^3/mm^3$) or CTC Grade 4 thrombocytopenia(platelet count of less than $25 \times 10^3/mm^3$).

The most common side effects of alpha interferon are:
flu-like syndrone
Neurotoxicity, including neuropsychiatric, neurosensory, and neuromotor,
Cardiopulmonary
Gastrointestinal, including nausea, vomiting, and/or diarreha
Hepatotoxicity, including elevations of bilirubin, transaminases, or alkaline phosphatase
Nephrotoxicity.

The invention claimed is:

1. A method for treating a malignant melanoma in a patient in need of such treating comprising administering temozolomide and interferon alpha 2b in amounts sufficient to eliminate or at least alleviate one or more of the signs or symptoms of the malignant melanoma.

2. The method of claim 1 wherein the amount of temozolomide administered is from 50 to 400 mg per $m^2$ of the patient'1s body surface area per day for a period of from 2 to 10 days and the amount of interferon alpha 2b administered is from 1 million to 25 million IU per $m^2$ of the patient's body surface area administered intraveneously or subcutaneously 1 to 7 times per week.

3. The method of claim 2 wherein beginning 28 to 42 days after the first day of the temozolomide administration period, the temozolomide administrations are repeated.

4. The method of claim 2 wherein the amount of temozolomide administered is from 75 to 300 mg per $m^2$ of the patient's body surface area per day for a period of from 3 to 8 days and the amount of interferon alpha 2b administered is from 5 million to 15 million IU per $m^2$ of the patient's body surface area administered intravenously or subcutaneously.

5. The method of claim 4 wherein beginning about 28 to 35 days after the first day of the temozolomide administration period, the temozolomide administrations are repeated.

6. The method of claim 4 wherein the amount of temozolomide administered is from 100 to 200 mg per $m^2$ of the patient's body surface area per day for a period of 5 days and the amount of interferon alpha 2b administered is from 7.5 million to 12.5 million IU per $m^2$ of the patient's body surface area administered intravenously or subcutaneously.

7. The method of claim 6 wherein beginning 28 days after the first day of the temozolomide administration period, the temozolomide administrations are repeated.

8. The method of claim 1 wherein the temozolomide is administered orally after the patient has fasted from food and liquids other than water for 4 hours before temozolomide administration and for 2 hours after temozolomide administration.

9. The method of claim 2 wherein the temozolomide is administered orally after the patient has fasted from food and liquids other than water for 4 hours before temozolomide administration and for 2 hours after temozolomide administration.

10. The method of claim 3 wherein the temozolomide is administered orally after the patient has fasted from food and liquids other than water for 4 hours before temozolomide administration and for 2 hours after temozolomide administration.

11. The method of claim 4 wherein the temozolomide is administered orally after the patient has fasted from food and liquids other than water for 4 hours before temozolomide administration and for 2 hours after temozolomide administration.

12. The method of claim 4 wherein the temozolomide is administered orally after the patient has fasted from food and liquids other than water for 4 hours before temozolomide administration and for 2 hours after temozolomide administration.

13. The method of claim 6 wherein the temozolomide is administered orally after the patient has fasted from food and liquids other than water for 4 hours before temozolomide administration and for 2 hours after temozolomide administration.

14. The method of claim 7 wherein the temozolomide is administered orally after the patient has fasted from food and liquids other than water for 4 hours before temozolomide administration and for 2 hours after temozolomide administration.

15. The method of claim 1 wherein the temozolomide is administered orally for a period of from 6 days to 6 weeks.

16. The method of claim 1 wherein the malignant melanoma is a malignant metastasized melanoma.

* * * * *

UNITED STATES PATENT AND TRADEMARK OFFICE
CERTIFICATE OF CORRECTION

PATENT NO.        : 7,294,332 B2
APPLICATION NO.   : 10/134183
DATED             : November 13, 2007
INVENTOR(S)       : Margaret H. Dugan It is certified that error appears in the above-identified patent and that said Letters Patent is hereby corrected as shown below:

In the Claims:

Col. 5, line 47: Replace "patient'1s" with -- patient's --.

Col. 6, line 38: Replace "claim 4" with -- claim 5 --.

Signed and Sealed this

Thirteenth Day of May, 2008

JON W. DUDAS
*Director of the United States Patent and Trademark Office*